(12) United States Patent
Castro Guzman et al.

(10) Patent No.: US 11,292,516 B2
(45) Date of Patent: Apr. 5, 2022

(54) ANTI-VIBRATION DRIVER ASSIST

(71) Applicant: Ford Motor Company, Dearborn, MI (US)

(72) Inventors: Christian Castro Guzman, Naucalpan (MX); Maria Fernanda Pulido Plauchud, Toluca (MX); Oswaldo Perez Barrera, Texcoco (MX)

(73) Assignee: FORD MOTOR COMPANY, Dearborn, MI (US)

( * ) Notice: Subject to any disclaimer, the term of this patent is extended or adjusted under 35 U.S.C. 154(b) by 253 days.

(21) Appl. No.: 16/468,744

(22) PCT Filed: Dec. 12, 2016

(86) PCT No.: PCT/US2016/066065
§ 371 (c)(1),
(2) Date: Jun. 12, 2019

(87) PCT Pub. No.: WO2018/111216
PCT Pub. Date: Jun. 21, 2018

(65) Prior Publication Data
US 2019/0315401 A1     Oct. 17, 2019

(51) Int. Cl.
*F16F 9/32* (2006.01)
*B62D 7/22* (2006.01)
(Continued)

(52) U.S. Cl.
CPC ............ *B62D 7/222* (2013.01); *A61B 5/1101* (2013.01); *A61B 5/4082* (2013.01);
(Continued)

(58) Field of Classification Search
CPC ......... B62D 7/222; B62D 1/04; A61B 5/1101; A61B 5/4082; A61B 5/6893;
(Continued)

(56) References Cited

U.S. PATENT DOCUMENTS 4,689,449 A    8/1987   Rosen
4,770,438 A *  9/1988   Sugasawa .......... B60G 17/0165
                                                    180/169
(Continued)

FOREIGN PATENT DOCUMENTS

DE    102014007538 A1    11/2014
KR       101148466 B1     5/2012
(Continued)

OTHER PUBLICATIONS

International Preliminary Report on Patentability dated Jun. 27, 2019 re Appl. No. PCT/US2016/0666065.
(Continued)

*Primary Examiner* — Zhen Y Wu
(74) *Attorney, Agent, or Firm* — Brandon Hicks; Bejin Bieneman PLC

(57) ABSTRACT

A vehicle anti-vibration device includes a vibration sensor programmed to detect vibrations and output a vibration signal representing the vibrations detected. The device further includes a motor that vibrates in accordance with a vibration dampening signal, a communication interface programmed to wirelessly transmit the vibration signal to a remote device, and a processor programmed to process the vibration signal and generate the vibration dampening signal to dampen the vibrations detected.

19 Claims, 5 Drawing Sheets

(51) Int. Cl.
| | | |
|---|---|---|
| *A61B 5/11* | (2006.01) | |
| *A61B 5/00* | (2006.01) | |
| *B62D 1/04* | (2006.01) | |
| *B62K 21/12* | (2006.01) | |
| *F16F 15/00* | (2006.01) | |

(52) U.S. Cl.
CPC .......... *A61B 5/6893* (2013.01); *A61B 5/0002* (2013.01); *A61B 2503/22* (2013.01); *B62D 1/04* (2013.01); *B62K 21/12* (2013.01); *F16F 15/005* (2013.01)

(58) Field of Classification Search
CPC .. A61B 5/0002; A61B 2503/22; B62K 21/12; F16F 15/005
USPC ...................................................... 188/266.7
See application file for complete search history.

(56) References Cited

U.S. PATENT DOCUMENTS

| | | | | |
|---|---|---|---|---|
| 5,528,913 | A | * | 6/1996 | Savkar .................... D06F 37/20 68/23.3 |
| 6,466,134 | B1 | * | 10/2002 | Ahearn .................. G07C 5/008 340/309.16 |
| 8,187,209 | B1 | | 5/2012 | Giuffrida |
| 8,264,458 | B2 | | 9/2012 | Cooper et al. |
| 8,632,097 | B1 | * | 1/2014 | Quinn ................... F16F 7/1017 280/771 |
| 9,414,776 | B2 | | 8/2016 | Sillay et al. |
| 9,469,329 | B1 | * | 10/2016 | Leanza .................. B60K 37/00 |
| 9,581,215 | B2 | * | 2/2017 | Ebana .................... B62D 7/222 |
| 2001/0032743 | A1 | | 10/2001 | Kamen et al. |
| 2002/0125084 | A1 | * | 9/2002 | Kreuzer ................ F16F 7/1005 188/267.1 |
| 2005/0173915 | A1 | * | 8/2005 | Stich ..................... F16F 15/005 280/779 |
| 2005/0228557 | A1 | | 10/2005 | Swan |
| 2007/0007069 | A1 | * | 1/2007 | Hamasaki ............. F16F 1/3732 180/417 |
| 2007/0235247 | A1 | * | 10/2007 | Hirakawa ............. B62D 5/0406 180/444 |
| 2008/0228354 | A1 | * | 9/2008 | Kimura ................ B62D 5/0463 701/42 |
| 2008/0235472 | A1 | * | 9/2008 | Ebata .................... G06F 3/0608 711/162 |
| 2013/0033018 | A1 | * | 2/2013 | Kiselis ..................... B60G 5/00 280/124.116 |
| 2013/0152721 | A1 | * | 6/2013 | Trendov .................. F16F 7/108 74/484 R |
| 2013/0240286 | A1 | * | 9/2013 | Asada ...................... B62D 5/06 180/417 |
| 2014/0032051 | A1 | * | 1/2014 | Ezoe ...................... B62D 6/001 701/42 |
| 2014/0053371 | A1 | * | 2/2014 | Feinstein ............... B62K 11/14 16/430 |
| 2014/0365074 | A1 | * | 12/2014 | Kim ..................... F16F 15/002 701/36 |
| 2015/0001773 | A1 | * | 1/2015 | Inoue .................... F16F 15/022 267/140.15 |
| 2015/0100221 | A1 | * | 4/2015 | Routledge ............... F01N 1/165 701/111 |
| 2015/0182160 | A1 | | 7/2015 | Kim et al. |
| 2015/0363983 | A1 | * | 12/2015 | Cunnings ............... G07C 5/008 701/29.1 |
| 2016/0009317 | A1 | * | 1/2016 | Evreinov ............... B62D 1/046 701/36 |
| 2016/0031481 | A1 | * | 2/2016 | Birsching ................ B62D 5/06 701/36 |
| 2016/0228640 | A1 | * | 8/2016 | Pindado ............. A61N 1/36139 |
| 2016/0312847 | A1 | * | 10/2016 | Suntsova .............. B64C 27/001 |
| 2016/0325776 | A1 | * | 11/2016 | Yamamoto ............... B62D 6/10 |
| 2016/0347345 | A1 | * | 12/2016 | Obayashi ............... B60Q 5/003 |
| 2016/0363518 | A1 | * | 12/2016 | Sever .................... G01M 5/0066 |
| 2017/0225633 | A1 | * | 8/2017 | Aoyagi ................. H02K 7/1853 |
| 2018/0053603 | A1 | * | 2/2018 | Al-Hazmi .............. H01G 4/206 |
| 2018/0062062 | A1 | * | 3/2018 | de Bonfim Gripp ....................... H01L 41/042 |
| 2018/0104984 | A1 | * | 4/2018 | Lim ....................... B60B 21/026 |
| 2018/0112734 | A1 | * | 4/2018 | Spencer ................. F16F 7/1011 |
| 2018/0118253 | A1 | * | 5/2018 | Minamiguchi .......... B62D 6/10 |
| 2018/0235472 | A1 | * | 8/2018 | Kim ...................... A61B 5/0051 |
| 2019/0100234 | A1 | * | 4/2019 | Kezobo .................. B62D 6/008 |

FOREIGN PATENT DOCUMENTS

| | | |
|---|---|---|
| WO | 2016102958 A1 | 6/2016 |
| WO | 2016154285 A1 | 9/2016 |
| WO | 2016154295 A1 | 9/2016 |

OTHER PUBLICATIONS

International Search Report and Written Opinion dated Apr. 27, 2017 re International Appl. PCT/US2016/066065.

\* cited by examiner

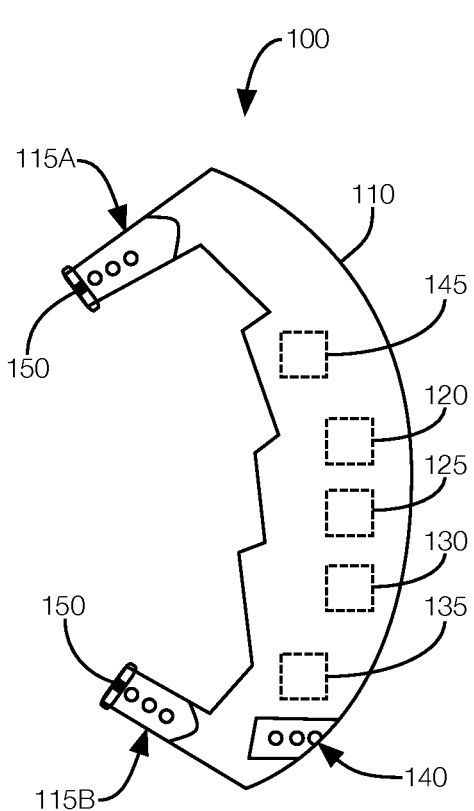
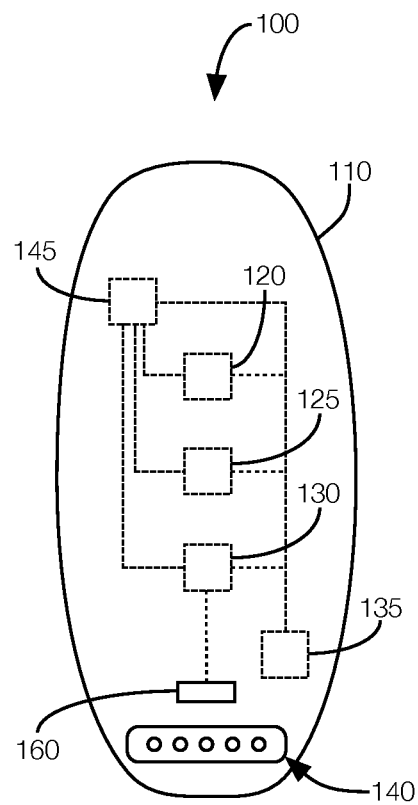
FIG. 1A
FIG. 1B

ANTI-VIBRATION DRIVER ASSIST

BACKGROUND

Operating an automobile requires certain fine and gross motor skills. Gross motor skills include moving one's foot to actuate the accelerator or brake pedal and using one's arms to turn the steering wheel. Fine motor skills include using one's fingers to provide a user input to, e.g., an infotainment system.

BRIEF DESCRIPTION OF THE DRAWINGS

FIGS. 1A-1D illustrate an example anti-vibration device for attachment to a steering wheel or motorcycle, bicycle, or scooter handlebars.

DETAILED DESCRIPTION

Degenerative central nervous system diseases, such as Parkinson's disease, and other neurological disorders can interfere with a vehicle driver's fine motor skills, gross motor skills, or both. For instance, degenerative diseases and other neurological disorders can cause involuntary muscle movements such as tremors. The tremors may make it difficult for those who suffer from such diseases to operate a motor vehicle, specifically, turning the steering wheel.

One way to mitigate tremors is with an anti-vibration device that attaches to the steering. The device includes a vibration sensor programmed to detect vibrations and output a vibration signal representing the vibrations detected. The device further includes a motor that vibrates in accordance with a vibration dampening signal, a communication interface programmed to wirelessly transmit the vibration signal to a remote device, and a processor programmed to process the vibration signal and generate the vibration dampening signal to dampen the vibrations detected. In some instances, the device can be incorporated into the steering wheel or handlebars for a motorcycle, bicycle, or scooter. Further, when incorporated into the steering wheel, the motor may be replaced by an electroactive stiffener that stiffens in accordance with a vibration dampening signal.

Moreover, by transmitting the vibration signal to a remote device, such as a user's smart phone, the user can see a visual representation of the severity of his or her condition. The user may share that data with his or her doctor so that the severity of the user's condition can be monitored.

The elements shown may take many different forms and include multiple and/or alternate components and facilities. The example components illustrated are not intended to be limiting. Indeed, additional or alternative components and/or implementations may be used. Further, the elements shown are not necessarily drawn to scale unless explicitly stated as such.

Figure 1C:
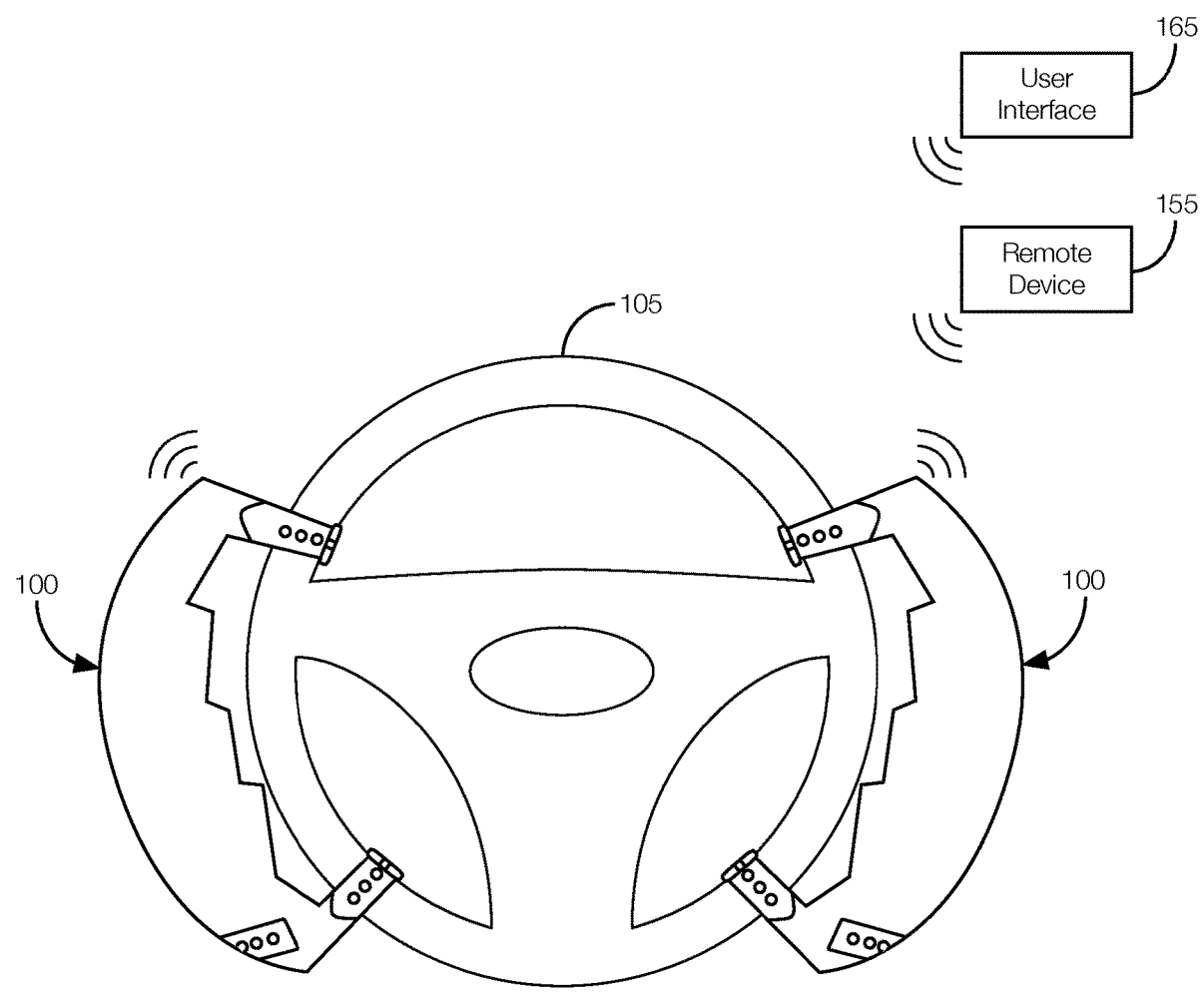
Figure 1D:
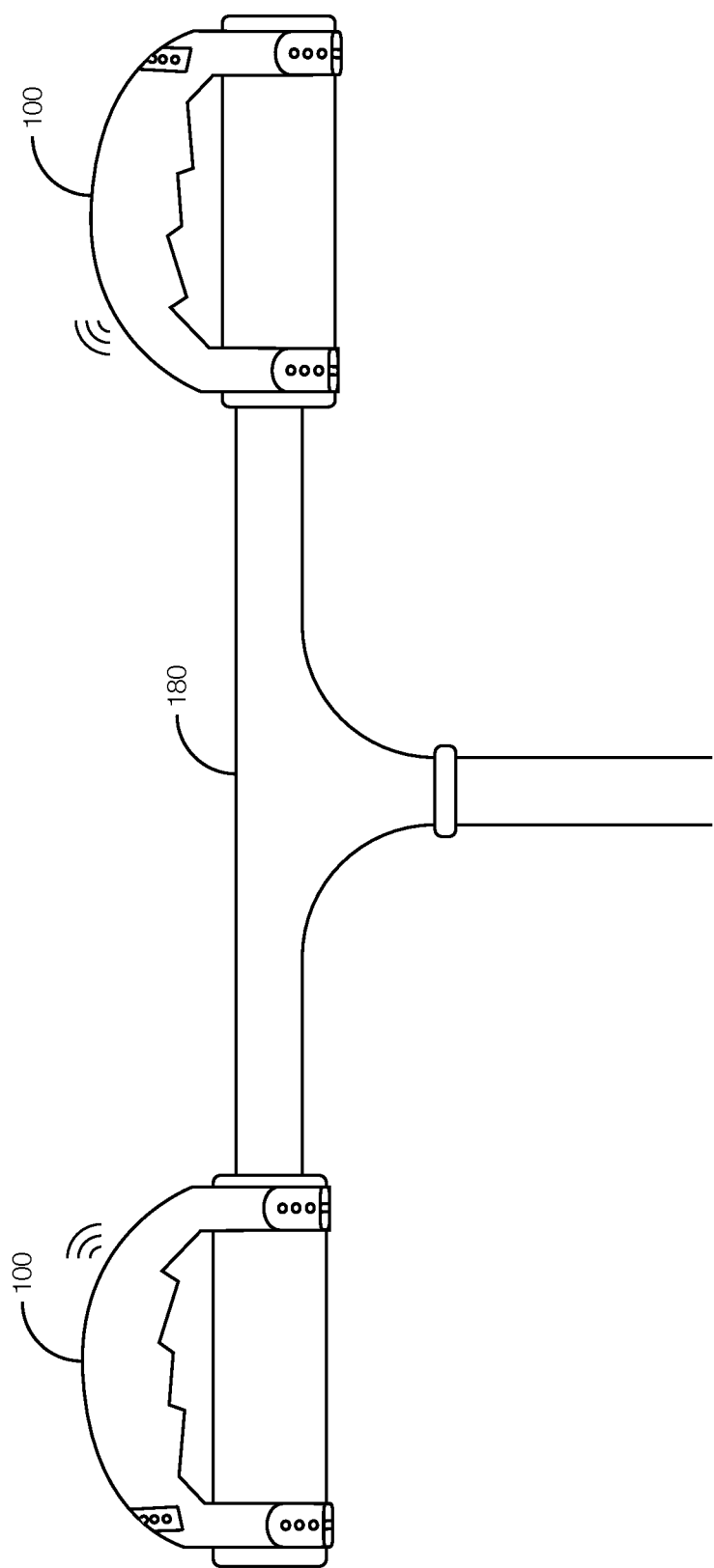

FIG. 1A shows a side view of an anti-vibration device 100. FIG. 1B shows a front view of the anti-vibration device 100. FIG. 1C shows the anti-vibration device 100 attached to a steering wheel 105. FIG. 1D shows the anti-vibration device 100 attached to motorcycle, bicycle, or scooter handlebars. As illustrated in FIGS. 1A-1D, the anti-vibration device 100 includes a housing 110, straps 115, a vibration sensor 120, a motor 125, a communication interface 130, a battery 135, status indicator lights 140, and a processor 145. The anti-vibration device 100 attaches to a steering wheel 105 (FIG. 1C) or handlebars 180 (FIG. 1D) and dampens vibrations that would otherwise be imparted to the steering wheel 105 or handlebars 180. Examples of such vibrations may include vibrations resulting from tremors due to a neurological disorder. Although shown in FIG. 1C as attached to the steering wheel 105, the anti-vibration device 100 may alternatively be attached to other vehicle devices, such as a turn signal lever, a wiper control lever, etc. Moreover, the anti-vibration device 100 may attach to a bicycle, scooter, or motorcycle handlebar 180 as shown in FIG. 1D.

The housing 110 is formed from a relatively rigid material such as plastic or rubber. The housing 110 houses or supports the other components of the anti-vibration device 100 including the straps 115, the vibration sensor 120, the motor 125, the communication interface 130, the battery 135, and the processor 145. In some instances, the housing 110 has an ergonomic shape and size to make it easier to hold. Further, at least part of the housing 110 may be rounded to follow the curvature of a steering wheel 105.

The straps 115, e.g., a first strap 115A and a second strap 115B, are formed from a relatively rigid material such as plastic or rubber. The straps 115 may each include a buckle 150 or clasp for attaching the strap to the steering wheel 105. The buckle 150 may have a frame, bar, and prong that engage the strap. Specifically, the prong may be disposed inside an opening defined by the strap when attached to the steering wheel 105. The bar and frame may help keep the prong engaged with the opening. Alternatively, the buckle 150 may be a snap-fit buckle.

The vibration sensor 120 is implemented via circuits, chips, or other electronic components that detect vibrations and output a vibration signal representing the vibrations detected. For instance, the vibration sensor 120 may include an accelerometer. The vibration sensor 120 receives an input when a driver is holding onto the anti-vibration device 100. The input may include vibrations caused by tremors due to the driver having a neurological disorder. The vibration sensor 120 may detect such tremors and output the vibration signal representing the magnitude and frequency of the tremors over time.

The motor 125 is an electric motor that receives a vibration dampening signal and vibrates according to the vibration dampening signal received. The motor 125 may be implemented via, e.g., a piezoelectric motor, a coin vibration motor (i.e., a shaftless or pancake vibration motor), an eccentric rotating mass motor (i.e., a motor with an off-center mass), or the like. In one possible approach, the motor 125 may vibrate with equal magnitude but opposite direction relative to the input to the vibration signal. By vibrating in this opposite way, the vibration of the motor 125 may dampen the vibrations detected by the vibration signal.

The communication interface 130 is implemented via circuits, chips, or other electronic components that can wirelessly transmit the vibration signal, or other data representing the vibration signal, to a remote device 155 such as a cell phone, tablet computer, laptop computer, cloud-based server, etc. In some instances, the communication interface 130 is programmed to transmit the vibration signal or other data representing the vibration signal to a component of a host vehicle, such as a user interface 165 (e.g., a vehicle infotainment system). In such instances, the communication interface 130 may pair with the user interface 165, the remote device 155, or both. The communication interface 130 may be programmed to communicate according to any number of wired or wireless telecommunication protocols. Examples of telecommunication protocols may include cellular communication protocols, satellite communication protocols, Bluetooth®, Bluetooth® Low Energy, Ethernet, a controller area network (CAN) bus, a universal serial bus (USB), etc. In some instances, the communication interface 130 includes an input/output port 160, such as a USB port, for providing a wired connection to the remote device 155. Thus, a user can plug his or her cell phone, tablet computer, laptop computer, etc., directly into and download data from the anti-vibration device 100.

The battery 135 is an energy storage device with one or more electrochemical cells. The electrochemical cells create a voltage differential, and current will flow from the battery 135 when provided with a load. The battery 135 may power any number of the components of the anti-vibration device 100 including the vibration sensor 120, the motor 125, the communication interface 130, the status indicator lights 140, and the processor 145. The battery 135 may be charged by, e.g., inserting a charging cable into the input/output port 160.

The status indicator lights 140 are small lights, such as light emitting diodes, that illuminate to provide a status of the anti-vibration device 100. The lights may illuminate with various colors or patterns to indicate that the anti-vibration device 100 is turned on, that the battery 135 has power, the state of charge of the battery 135, whether the communication interface 130 is paired with any remote devices 155, whether the communication interface 130 is transmitting data, whether the vibration sensors 120 are receiving vibration signals, the anti-vibration signals, etc.

The processor 145 is implemented via circuits, chips, or other electronic components that are programmable with computer-executable instructions stored in a local or remote memory. The processor 145 is programmed to receive the vibration signals output by the vibration sensor 120, process the vibration signals, generate the vibration dampening signal, and output the vibration dampening signal to the motor 125. The processor 145 may generate the vibration dampening signal to be equal but opposite relative to the vibration signal. That is, the vibration dampening signal may be generated by the processor 145 to have an equal amplitude (magnitude) but opposite direction relative to the vibration signal. In some instances, however, the vibration dampening signal may be generated independent of the vibration signal. That is, the vibration dampening signal may simply cause the anti-vibration device 100 to vibrate regardless of how the user's tremors act on the anti-vibration device 100. In this instance, the processor 145 may detect the vibration signal (indicating that the user is experiencing tremors) and generate and output the vibration dampening signal to the motor 125 to make the anti-vibration device 100 vibrate. The vibrations themselves may help the user stabilize his or her hands.

Moreover, the processor 145 may be programmed to command the communication interface 130 to transmit the vibration signal to a user interface 165 located in the passenger compartment of a vehicle, to the remote device 155, or both, along with historical data (i.e., the day and time the vibration signals were captured). The processor 145 may be further programmed to command the communication interface 130 to transmit the vibration dampening signal to the user interface 165 or to the remote device 155 with historical data. That way, a user of the anti-vibration device 100 can see a history of the vibration signal and the amount of dampening applied. The user can share that data with his or her physician who can determine whether the user's tremors are improving or getting worse over time, and if the dampening is sufficient to permit the user to continue to drive.

If multiple anti-vibration devices 100 are used, each may independently transmit data to the remote device 155, the user interface 165, or both. The data may include which device transmitted the data so, e.g., the user knows whether it was his or her right hand or left hand that caused the vibrations. The data, when presented on the user interface 165 or remote device 155 may indicate whether the vibration signal applies to the user's right hand or left hand.

FIG. 1D illustrates the anti-vibration device 100 located on the handlebars 180 of a motorcycle, bicycle, scooter, etc. Thus, the anti-vibration device 100 is not limited to a steering wheel. The anti-vibration device 100 shown in FIG. 2 includes the same components as discussed above. Thus, the anti-vibration device 100 of FIG. 2 may detect vibrations, dampen the vibrations by vibrating the motor 125, and communicate the vibration signal to a remote device 155. Also, the housing 110 may have a slightly different shape to better accommodate the handlebars 180 as opposed to the contours of a steering wheel 105.

Figure 2:
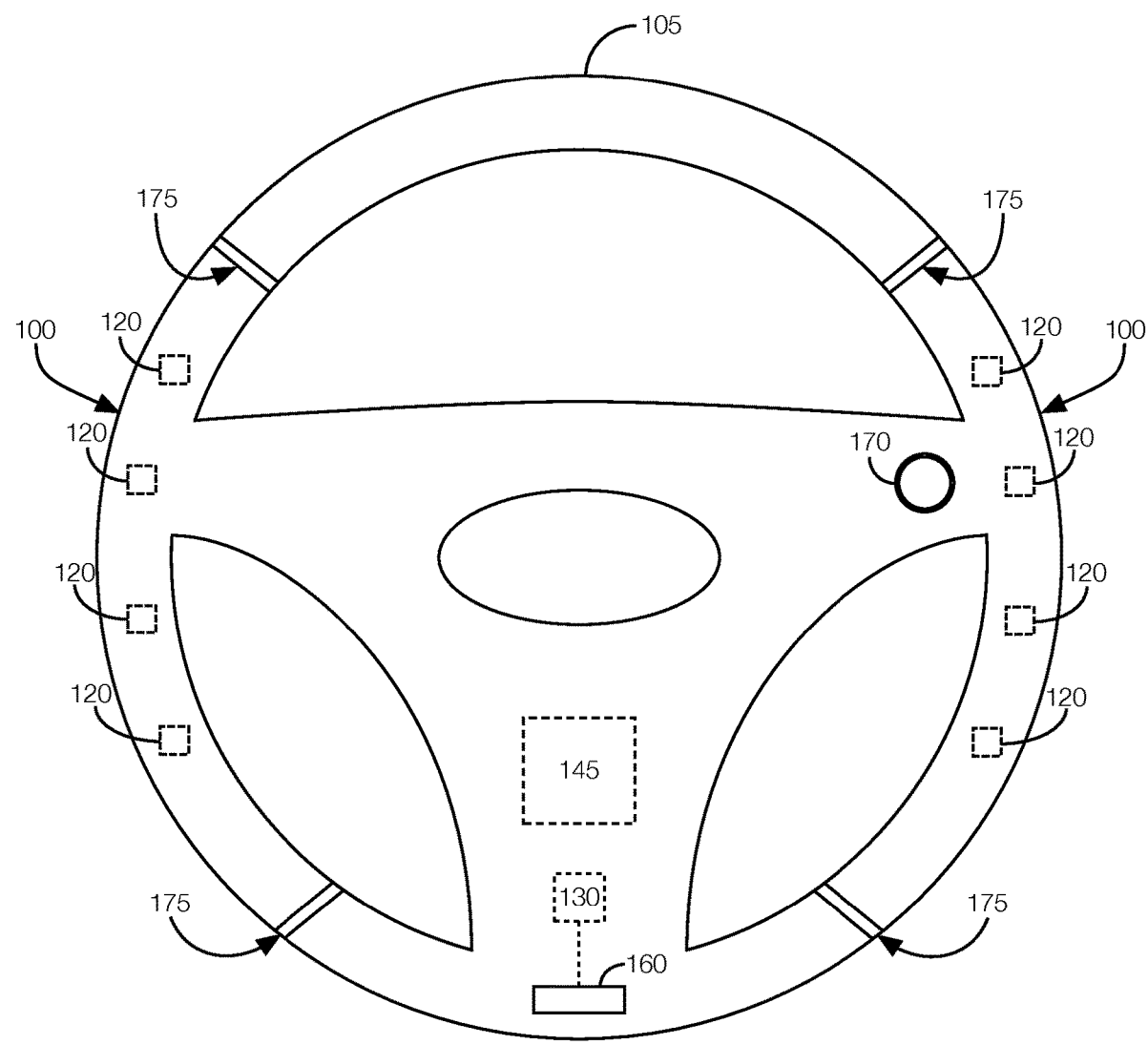
FIG. 2 illustrates a steering wheel with the components of the anti-vibration device incorporated into the steering wheel.
Figure 3:
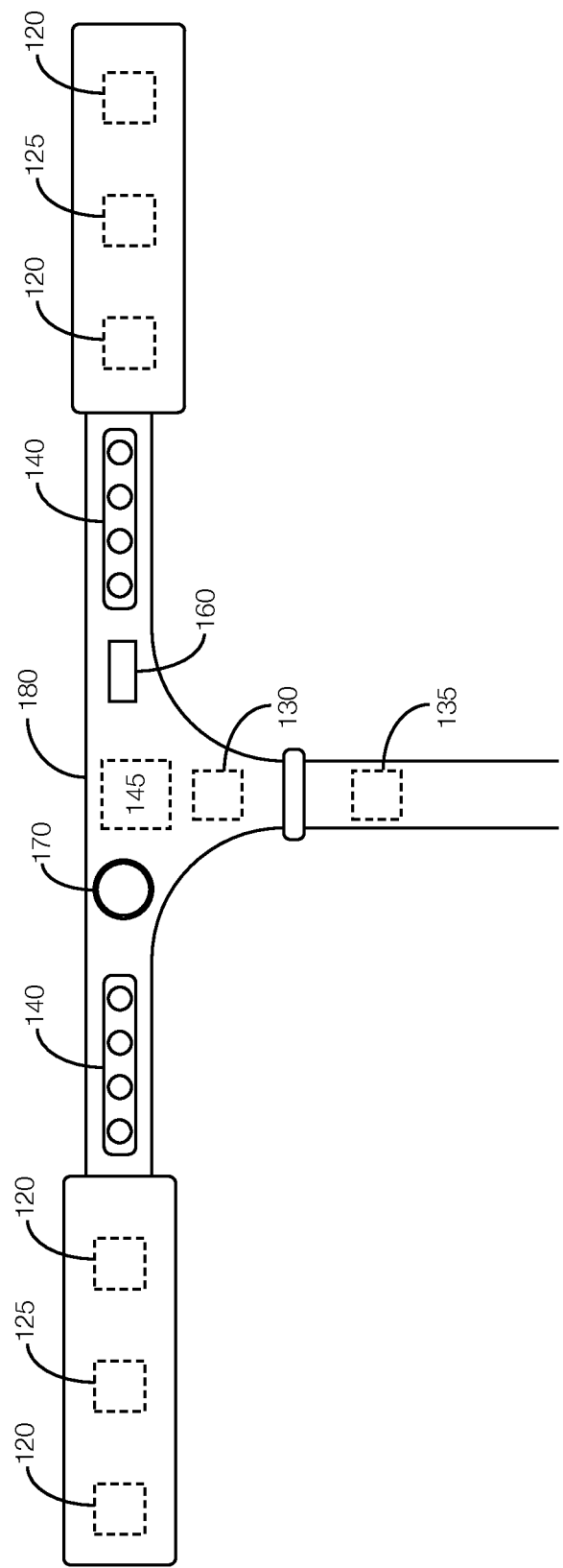
FIG. 3 illustrates handlebars with components of the anti-vibration device incorporated into the handlebars.

FIGS. 2 and 3 illustrate an example steering wheel 105 (FIG. 2) and handlebars 180 (FIG. 3) with the components of the anti-vibration device 100 incorporated into the steering wheel 105 and handlebars 180, respectively. As shown in FIG. 2, the steering wheel 105 includes (i.e., houses) the vibration sensors 120, the communication interface 130 (including the input/output port 160, as shown), and the processor 145 discussed above. The steering wheel 105 may omit the status indicator lights 140 and the battery 135. The status indicator lights 140 may (but need not) be omitted since the components of the anti-vibration device 100 may be hard-wired to various vehicle systems. Thus, the user interface 165 may present the status anti-vibration device 100. Moreover, the battery 135 may be omitted since the components of the anti-vibration device 100 may be powered by the accessory battery located on the vehicle. Further, the steering wheel 105 may use the motor 125 described above. Also, when incorporated into the steering wheel 105, a button or switch 170 may be used to turn the anti-vibration device 100 on or off.

Alternatively, instead of motors 125, the steering wheel 105 may include electroactive stiffeners 175 formed from an electroactive polymer with an adjustable stiffness. The stiffness of the electroactive stiffener 175 may be directly proportional to an electric field applied to the electroactive stiffener 175. That is, the electroactive stiffener 175 may stiffen as more electrical energy is applied to the electroactive stiffener 175. As such, the processor 145 may be programmed to decrease the stiffness of the electroactive stiffener 175 to dampen the vibrations detected. That is, the processor 145 may be programmed to reduce the stiffness as the magnitude of the vibration signal increases and increase the stiffness as the magnitude of the vibration signal decreases.

The electroactive stiffeners 175 may be located throughout the steering wheel 105. Moreover, the electroactive stiffeners 175 may be grouped in pairs and may be incorporated into the steering wheel 105 at locations where the user's hands will hold the steering wheel 105 between two electroactive stiffeners 175 in a pair. The processor 145 may be programmed to similarly control each electroactive stiffener 175 in a pair, but not necessarily control the electroactive stiffeners 175 in the other pair the same way. Thus, if a user's left hand is providing greater vibration input than the user's right hand, the processor 145 may reduce the stiffness of the electroactive stiffeners 175 on the left side of the steering wheel 105 (i.e., in the left pair) while keeping the stiffness of the electroactive stiffeners 175 on the right side of the steering wheel 105 (i.e., the right pair) at a normal or high stiffness.

Further, the electroactive stiffeners 175 may be relatively thin so that only inadvertent tremors are absorbed by the electroactive stiffeners 175. In other words, the processor 145 will not attempt to reduce the stiffness to absorb a purposeful attempt to turn the steering wheel 105. Further, the processor 145 may detect that the user intends to turn the steering wheel 105 based on, e.g., an acceleration sensor or encoder located in or used in accordance with the steering wheel 105. In such instances, the processor 145 may output a signal to stiffen all the electroactive stiffeners 175.

Although only a single processor 145 is shown in FIG. 2, different processors 145 may monitor and process signals from different sets of vibration sensors 120. For instance, one processor 145 may process the signals output by the vibration sensors 120 and control the electroactive stiffeners 175 on the left side of the steering wheel 105 and another processor 145 may process the signals output by the vibration sensors 120 and control the electroactive stiffeners 175 on the right side of the steering wheel 105.

As shown in FIG. 3, the handlebars 180 include (i.e., house) the vibration sensors 120, the communication interface 130 (including the input/output port 160, as shown), and the processor 145 discussed above. The status indicator lights 140 and battery 135 are also present, although the battery 135 may be omitted since components of the anti-vibration device 100 may be powered by an on-board battery (of, e.g., a motorcycle, electric bicycle, electric scooter) or the conversion of rotational energy applied to, e.g., the bicycle pedals into electrical energy. Also, when incorporated into the handlebars 180, a button or switch 170 may be used to turn the anti-vibration device 100 on or off.

The anti-vibration device 100, whether as an attachment to or incorporated into a steering wheel 105 or handlebars 180, can mitigate difficulty driving for people with tremors caused by, e.g., degenerative neurological diseases. Moreover, by transmitting data, such as the vibration signal, the vibration dampening signal, and historical information, to a remote device 155, such as a user's smart phone, or to a user interface 165 located in the vehicle, the user can see a visual representation of the severity of his or her condition and how well the anti-vibration device 100 is working. The user may share that data with his or her doctor so that the severity of the user's condition and the effectiveness of the anti-vibration device 100 can be monitored.

In general, the computing systems and/or devices described may employ any of a number of computer operating systems, including, but by no means limited to, versions and/or varieties of the Ford Sync® application, AppLink/Smart Device Link middleware, the Microsoft Automotive® operating system, the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX and iOS operating systems distributed by Apple Inc. of Cupertino, Calif., the BlackBerry OS distributed by Blackberry, Ltd. of Waterloo, Canada, and the Android operating system developed by Google, Inc. and the Open Handset Alliance, or the QNX® CAR Platform for Infotainment offered by QNX Software Systems. Examples of computing devices include, without limitation, an on-board vehicle computer, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. A vehicle anti-vibration device comprising:
   a vibration sensor programmed to detect vibrations and output a vibration signal representing the vibrations detected;
   an electroactive stiffener that stiffens in accordance with a vibration dampening signal;
   a communication interface programmed to wirelessly transmit the vibration signal to a remote device; and
   a processor programmed to process the vibration signal and generate the vibration dampening signal to dampen the vibrations detected;
   the processor is further programmed to decrease the stiffness of the electroactive stiffener to dampen the vibrations detected.

2. The vehicle anti-vibration device of claim 1, wherein the processor is programmed to output the vibration signal to a user interface located in a passenger compartment of a vehicle.

3. The vehicle anti-vibration device of claim 1, further comprising:
   a housing; and
   a first strap disposed on the housing for attaching the vehicle anti-vibration device to a steering wheel.

4. The vehicle anti-vibration device of claim 3, further comprising a second strap disposed on the housing and spaced from the first strap.

5. The vehicle anti-vibration device of claim 1, further comprising a housing, wherein the vibration sensor, the electroactive stiffener, the communication interface, and the processor are located inside the housing.

6. The vehicle anti-vibration device of claim 1, wherein the communication interface includes an input/output port for connecting to the remote device.

7. The vehicle anti-vibration device of claim 1, further comprising a battery that outputs electrical energy to at least one of the vibration sensor, the communication interface, and the processor.

8. The vehicle anti-vibration device of claim 1, wherein the processor is programmed to command the communication interface to transmit the vibration signal to the remote device.

9. The vehicle anti-vibration device of claim 1, wherein the processor is programmed to command the communication interface to transmit historical data to the remote device with the vibration signal.

10. A vehicle steering wheel comprising:
    at least one vibration sensor programmed to detect vibrations and output a vibration signal representing the vibrations detected;
    an electroactive stiffener that stiffens in accordance with a vibration dampening signal;
    a communication interface programmed to wirelessly transmit the vibration signal to a remote device; and
    a processor programmed to process the vibration signal and generate the vibration dampening signal to dampen the vibrations detected;
    the processor is further programmed to decrease the stiffness of the electroactive stiffener to dampen the vibrations detected.

11. The vehicle steering wheel of claim 10, wherein the processor is programmed to output the vibration signal to a user interface located in a passenger compartment of a vehicle.

12. The vehicle steering wheel of claim 10, wherein the electroactive stiffener is formed from an electroactive polymer having a stiffness that increases in accordance with an electric field.

13. The vehicle steering wheel of claim 10, wherein the communication interface includes an input/output port for connecting to the remote device.

14. The vehicle steering wheel of claim 10, further comprising a battery that outputs electrical energy to at least one of the vibration sensor, the communication interface, and the processor.

15. The vehicle steering wheel of claim 10, wherein the processor is programmed to command the communication interface to transmit the vibration signal to the remote device.

16. The vehicle steering wheel of claim 10, wherein the processor is programmed to command the communication interface to transmit historical data to the remote device with the vibration signal.

17. A handlebar comprising:
at least one vibration sensor programmed to detect vibrations and output a vibration signal representing the vibrations detected;
an electroactive stiffener that stiffens in accordance with a vibration dampening signal;
a communication interface programmed to wirelessly transmit the vibration signal to a remote device; and
a processor programmed to process the vibration signal and generate the vibration dampening signal to dampen the vibrations detected;
the processor is further programmed to decrease the stiffness of the electroactive stiffener to dampen the vibrations detected.

18. The handlebar of claim 17, wherein the communication interface includes an input/output port for connecting to the remote device.

19. The handlebar of claim 17, wherein the processor is programmed to command the communication interface to transmit the vibration signal and historical data to the remote device.

\* \* \* \* \*